US006490475B1

(12) United States Patent
Seeley et al.

(10) Patent No.: US 6,490,475 B1
(45) Date of Patent: Dec. 3, 2002

(54) FLUOROSCOPIC TRACKING AND VISUALIZATION SYSTEM

(75) Inventors: Teresa Seeley, Littleton, MA (US); Faith Lin, Lexington, MA (US); Tina Kapur, Andover, MA (US); Gene Gregerson, Bolton, MA (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/560,608

(22) Filed: Apr. 28, 2000

(51) Int. Cl.$^7$ ................................................. A61B 5/05
(52) U.S. Cl. ...................... 600/426; 600/427; 600/429; 600/431; 606/130; 378/6; 378/21; 378/41; 378/42
(58) Field of Search ................................. 600/407, 426, 600/425, 421, 427, 429; 606/130, 431; 250/362, 363.01, 363.02, 363.03, 363.04, 363.05, 363.07, 363.09, 368, 370.08, 370.09, 370.1, 4, 550; 378/6, 21, 41, 42, 44, 46, 62, 63, 68

(56) References Cited

U.S. PATENT DOCUMENTS

| | | | | |
|---|---|---|---|---|
| 5,823,958 A | * | 10/1998 | Truppe | 600/426 |
| 6,006,126 A | * | 12/1999 | Cosman | 600/426 |
| 6,081,577 A | * | 6/2000 | Webber | 378/23 |
| 6,097,994 A | * | 8/2000 | Nevab et al. | 700/245 |
| 6,149,592 A | * | 11/2000 | Yanof et al. | 600/427 |

* cited by examiner

Primary Examiner—Marvin Lateef
Assistant Examiner—Jeoyuh Lin
(74) Attorney, Agent, or Firm—McAndrews, Held & Malloy, Ltd.; Peter J. Vogel; Michael A. Dellapenna

(57) ABSTRACT

A system employs a tracker and a set of substantially non-shadowing point markers, arranged in a fixed pattern or set in a fluoroscope calibration fixture that is imaged in each shot. The fixture is preferably affixed to the image detector of the fluoroscope, and tracking elements secured with respect to the fixture and at least one of a tool and the patient, provide respective position data irrespective of movement. A marker detection module identifies markers imaged in each shot, and a processor applies the known marker positions to model the projection geometry, e.g., camera axis and focus, for the shot and, together with the tracked tool position, form a corrected tool navigation image. In one embodiment an inverting distortion correction converts the tracked or actual location of the tool and displays the tool on the fluoroscopic image to guide the surgeon in tool navigation. In another aspect of the invention, the fluoroscope takes a series of frames while rotating in a plane about the patient, and the camera models derived from the marker images in each frame are applied to define a common center and coordinate axes in the imaged tissue region to which all of the fluoroscope view may be registered. The processor then filters and back-projects the image data or otherwise forms a volume image data set corresponding to the region of tissue being imaged, and desired fluoro-CT planar images of a the imaged patient volume are constructed from this data set. Planes may then be constructed and displayed without requiring complex tracking and image correlation systems previously needed for operating-room management of MRI, CT or PET study image data. Further, the fluoro-CT images thus constructed may be directly registered to preoperative MRI, CT or PET 3D image data, or may obviate the need for such preoperative imaging. Preferably, the tracker employs electromagnetic tracking elements, as shown for example in U.S. Pat. No. 5,967,980, to generate and/or detect electromagnetic field components unobstructed by the patient and intervening structures, and to determine coordinates directly referenced to the patient, the tool or the camera. The calibration fixture may be implemented with BBs in a radiolucent block of structural foam, and/or may be implemented by microlithographic techniques, in which case magnetic tracking elements may be simultaneously formed in registry with the markers on a sheet that mounts to the camera, is incorporated in a radiographic support table, or otherwise positioned to be imaged in each shot.

10 Claims, 10 Drawing Sheets

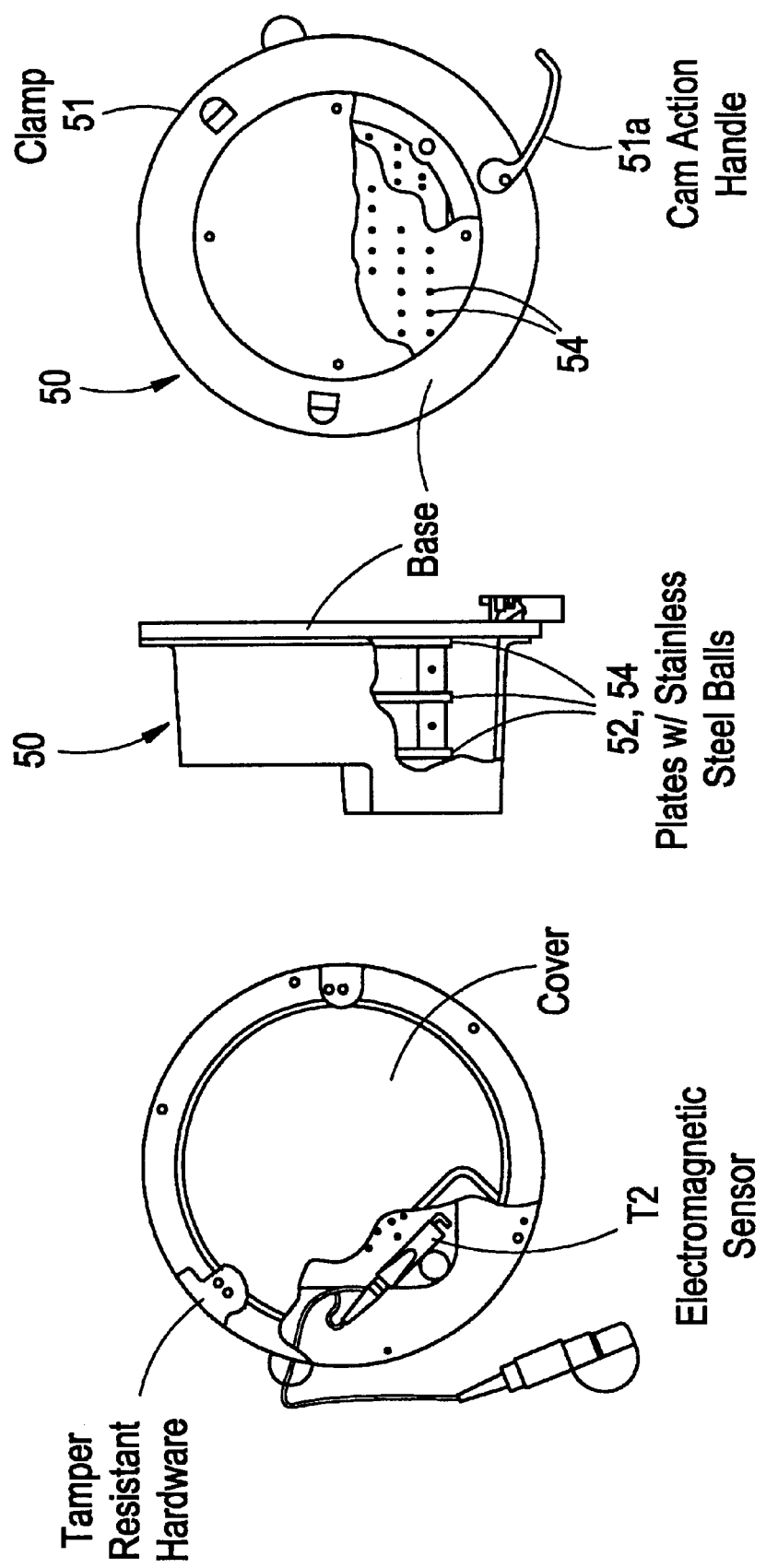

FLUOROSCOPIC TRACKING AND VISUALIZATION SYSTEM

BACKGROUND

The present invention relates to medical and surgical imaging, and in particular to intraoperative or perioperative imaging in which images are formed of a region of the patient's body and a surgical tool or instrument is applied thereto, and the images aid in an ongoing procedure. It is of a special utility in surgical procedures such as brain surgery and arthroscopic procedures on the knee, wrist, shoulder or spine, as well as certain types of angiography, cardiac procedures, interventional radiology and biopsies in which x-ray images may be taken to display, correct the position of, or otherwise navigate a tool or instrument involved in the procedure.

Several areas of surgery have required very precise planning and control for the placement of an elongated probe or other article in tissue or bone that is internal or difficult to view directly. In particular, for brain surgery, stereotactic frames to define the entry point, probe angle and probe depth are used to access a site in the brain, generally in conjunction with previously compiled three-dimensional diagnostic images such as MRI, PET or CT scan images which provide accurate tissue images. For placement of pedicle screws in the spine, where visual and fluoroscopic imaging directions cannot capture an axial view necessary to center the profile of an insertion path in bone, such systems have also been useful.

When used with existing CT, PET or MRI image sets, these previously recorded diagnostic image sets themselves define a three dimensional rectilinear coordinate system, by virtue of their precision scan formation or the spatial mathematics of their reconstruction algorithms. However, it may be necessary to correlate the available fluoroscopic views and anatomical features visible from the surface or in fluoroscopic images with features in the 3-D diagnostic images and with the external coordinates of the tools being employed. This is often done by providing implanted fiducials, and adding externally visible or trackable markers that may be imaged, and using a keyboard or mouse to identify fiducials in the various images, and thus identify common sets of coordinate registration points in the different images, that may also be trackable in an automated way by an external coordinate measurement device, such as a suitably programmed off-the-shelf optical tracking assembly. Instead of imageable fiducials, which may for example be imaged in both fluoroscopic and MRI or CT images, such systems can also operate to a large extent with simple optical tracking of the surgical tool, and may employ an initialization protocol wherein the surgeon touches or points at a number of bony prominences or other recognizable anatomic features in order to define the external coordinates in relation to the patient anatomy and to initiate software tracking of those features.

Generally, systems of this type operate with an image display which is positioned in the surgeon's field of view, and which displays a few panels such as a selected MRI image and several x-ray or fluoroscopic views taken from different angles. The three-dimensional diagnostic images typically have a spatial resolution that is both rectilinear and accurate to within a very small tolerance, e.g., to within one millimeter or less. The fluoroscopic views by contrast are distorted, and they are shadowgraphic in that they represent the density of all tissue through which the conical x-ray beam has passed. In tool navigation systems of this type, the display visible to the surgeon may show an image of the surgical tool, biopsy instrument, pedicle screw, probe or the like projected onto a fluoroscopic image, so that the surgeon may visualize the orientation of the surgical instrument in relation to the imaged patient anatomy, while an appropriate reconstructed CT or MRI image, which may correspond to the tracked coordinates of the probe tip, is also displayed.

Among the systems which have been proposed for effecting such displays, many rely on closely tracking the position and orientation of the surgical instrument in external coordinates. The various sets of coordinates may be defined by robotic mechanical links and encoders, or more usually, are defined by a fixed patient support, two or more receivers such as video cameras which may be fixed to the support, and a plurality of signaling elements attached to a guide or frame on the surgical instrument that enable the position and orientation of the tool with respect to the patient support and camera frame to be automatically determined by triangulation, so that various transformations between respective coordinates may be computed. Three-dimensional tracking systems employing two video cameras and a plurality of emitters or other position signaling elements have long been commercially available and are readily adapted to such operating room systems. Similar systems may also determine external position coordinates using commercially available acoustic ranging systems in which three or more acoustic emitters are actuated and their sounds detected at plural receivers to determine their relative distances from the detecting assemblies, and thus define by simple triangulation the position and orientation of the frames or supports on which the emitters are mounted. When tracked fiducials appear in the diagnostic images, it is possible to define a transformation between operating room coordinates and the coordinates of the image.

In general, the feasibility or utility of a system of this type depends on a number of factors such as cost, accuracy, dependability, ease of use, speed of operation and the like. Intraoperative x-ray images taken by C-arm fluoroscopes alone have both a high degree of distortion and a low degree of repeatability, due largely to deformations of the basic source and camera assembly, and to intrinsic variability of positioning and image distortion properties of the camera. In an intraoperative sterile field, such devices must be draped, which may impair optical or acoustic signal paths of the signal elements they employ to track the patient, tool or camera.

More recently, a number of systems have been proposed in which the accuracy of the 3-D diagnostic data image sets is exploited to enhance accuracy of operating room images, by matching these 3-D images to patterns appearing in intraoperative fluoroscope images. These systems may require tracking and matching edge profiles of bones, morphologically deforming one image onto another to determine a coordinate transform, or other correlation process. The procedure of correlating the lesser quality and non-planar fluoroscopic images with planes in the 3-D image data sets may be time-consuming, and in those techniques that rely on fiducials or added markers, the processing necessary to identify and correlate markers between various sets of images may require the surgeon to follow a lengthy initialization protocol, or may be a slow and computationally intensive procedure. All of these factors have affected the speed and utility of intraoperative image guidance or navigation systems.

Correlation of patient anatomy or intraoperative fluoroscopic images with precompiled 3-D diagnostic image data sets may also be complicated by intervening movement of the imaged structures, particularly soft tissue structures, between the times of original imaging and the intraoperative procedure. Thus, transformations between three or more coordinate systems for two sets of images and the physical coordinates in the operating room may require a large number of registration points to provide an effective correlation. For spinal tracking to position pedicle screws it may be necessary to initialize the tracking assembly on ten or more points on a single vertebra to achieve suitable accuracy. In cases where a growing tumor or evolving condition actually changes the tissue dimension or position between imaging sessions, further confounding factors may appear.

When the purpose of image guided tracking is to define an operation on a rigid or bony structure near the surface, as is the case in placing pedicle screws in the spine, the registration may alternatively be effected without ongoing reference to tracking images, by using a computer modeling procedure in which a tool tip is touched to and initialized on each of several bony prominences to establish their coordinates and disposition, after which movement of the spine as a whole is modeled by optically initially registering and then tracking the tool in relation to the position of those prominences, while mechanically modeling a virtual representation of the spine with a tracking element or frame attached to the spine. Such a procedure dispenses with the time-consuming and computationally intensive correlation of different image sets from different sources, and, by substituting optical tracking of points, may eliminate or reduce the number of x-ray exposures required to effectively determine the tool position in relation to the patient anatomy with the required degree of precision.

However, each of the foregoing approaches, correlating high quality image data sets with more distorted shadow-graphic projection images and using tracking data to show tool position, or fixing a finite set of points on a dynamic anatomical model on which extrinsically detected tool coordinates are superimposed, results in a process whereby machine calculations produce either a synthetic image or select an existing data base diagnostic plane to guide the surgeon in relation to current tool position. While various jigs and proprietary subassemblies have been devised to make each individual coordinate sensing or image handling system easier to use or reasonably reliable, the field remains unnecessarily complex. Not only do systems often require correlation of diverse sets of images and extensive point-by-point initialization of the operating, tracking and image space coordinates or features, but they are subject to constraints due to the proprietary restrictions of diverse hardware manufacturers, the physical limitations imposed by tracking systems and the complex programming task of interfacing with many different image sources in addition to determining their scale, orientation, and relationship to other images and coordinates of the system.

Several proposals have been made that fluoroscope images be corrected to enhance their accuracy. This is a complex undertaking, since the nature of the fluoroscope's 3D to 2D projective imaging results in loss of a great deal of information in each shot, so the reverse transformation is highly underdetermined. Changes in imaging parameters due to camera and source position and orientation that occur with each shot further complicate the problem. This area has been addressed to some extent by one manufacturer which has provided a more rigid and isocentric C-arm structure. The added positional precision of that imaging system offers the prospect that, by taking a large set of fluoroscopic shots of an immobilized patient composed under determined conditions, one may be able to undertake some form of planar image reconstruction. However, this appears to be computationally very expensive, and the current state of the art suggests that while it may be possible to produce corrected fluoroscopic image data sets with somewhat less costly equipment than that required for conventional CT imaging, intra-operative fluoroscopic image guidance will continue to require access to MRI, PET or CT data sets, and to rely on extensive surgical input and set-up for tracking systems that allow position or image correlations to be performed.

Thus, it remains highly desirable to utilize simple, low-dose and low cost fluoroscope images for surgical guidance, yet also to achieve enhanced accuracy for critical tool positioning.

It would be desirable to provide an improved image guided navigation system for a surgical instrument.

It would also be desirable to provide such an image guided system which operates with a C-arm fluoroscope to produce enhanced images and information.

It would also be desirable to provide an image-guided surgical navigation system adaptable to a fluoroscope that accurately depicts tool position.

SUMMARY OF THE INVENTION

One or more of the foregoing features and other desirable ends are achieved in a method or system of the present invention wherein an x-ray imaging machine of movable angulation, such as a fluoroscope, is operated to form reference or navigation images of a patient undergoing a procedure. A tracking system employs a tracking element affixed to each of the imaging machine and tool, and preferably to the patient as well, to provide respective position data for the tool, the fluoroscope and patient, while a fixed volume array of markers, which is also tracked, is imaged in each frame. Preferably the array of markers is affixed to the detector assembly of the imaging machine, where a single tracking element determines position of the fluoroscope and entire array of markers. The fluoroscope may itself also provide further shot-specific indexing or identification data of conventional type, such as time, settings or the like. A processor then applies the position data from the tracking system, and operates on the imaged markers to produce a correct tool navigation image for surgical guidance.

The markers are preferably arranged in a known pattern of substantially non-shadowing point elements positioned in different planes. These may be rigidly spaced apart in a predefined configuration in an assembly attached to the fluoroscope, so that the physical position of each marker is known exactly in a fixed fluoroscope-based coordinate system, and the positions may, for example, be stored in a table. A single tracking element may be affixed on the marker assembly, which may in turn be locked in a fixed position on the fluoroscope, so that the fluoroscope and marker positions are known in relation to the tool and the patient. Alternatively, one or more separate arrays of markers may be independently positioned and each tracked by a separate tracking element.

In each fluoroscopic image, the processor identifies a subset of the markers and recovers geometric camera calibration parameters from the imaged marker positions. These calibration parameters then allow accurate reference between the recorded image and the tool and patient coordinates measured by the trackers. The processor may also receive patient identification data of a conventional type to display or record with the shot. In one embodiment the processor computes the calibration as well as geometric distortion due to the imaging process, and converts the tracked or actual location of the tool to a distorted tool image position at which the display projects a representation of the tool onto the fluoroscopic image to guide the surgeon in tool navigation.

In this aspect of the invention, the processor identifies markers in the image, and employs the geometry of the identified markers to model the effective source and camera projection geometry each time a shot is taken, e.g., to effectively define its focus and imaging characteristics for each frame. These parameters are then used to compute the projection of the tool in the fluoroscope image.

In yet a further aspect of the invention, the fluoroscope is operated to take a series of shots in progressively varying orientations and positions as the camera and source are moved about the patient. Accurate calibration for multiple images is then employed to allow three-dimensional reconstruction of the image data. The processor applies a reconstruction operation or procedure, for example, back projection of the registered images to form a volume image data set, e.g., a three dimensional set of image density values of a tissue volume. The initial set of fluoroscopic images may, for example, be acquired by taking a series of views rotating the fluoroscope in a fixed plane about a target region of tissue. A common center and coordinate axes are determined for the reconstructed volume, such that the volume image data set constructed from the images corresponds to the target region. Image planes are then directly constructed and displayed from this volume image data set.

The resultant fluoro-CT images are geometrically comparable to conventional diagnostic image sets of the imaged volume, and obviate the need for complex tracking and image correlation systems otherwise proposed or required for operating-room management and display of preoperatively acquired volumetric data sets with intraoperative fluoro images. In accordance with a still further aspect of the invention, this reconstructed fluoro-CT data set is then registered to or transformed to the image space coordinates of a preoperative PET, MRI or CT data set for simultaneous display of both sets of images. In other embodiments, the system of the present invention may be used simply for the purpose of intraoperatively registering preoperative 3D image data to the patient tissue. In accordance with this aspect of the invention, a set of fluoro-CT image data is constructed as described above, and these are registered to preoperative 3D image data by mutual information, contour matching or other correlation procedure. This provides a direct registration of the preoperative data to tracking coordinates without requiring the surgeon to place and image fiducials, touch and enter skeletal or surface registration points, or perform invasive pre-operation image registration protocols.

The tracking elements of the tracking system may comprise various position-indicating elements or markers which operate optically, ultrasonically, electromagnetically or otherwise, and the tracking system itself may include hybrid software-mediated elements or steps wherein a pointer or tool of defined geometry is tracked as it touches fiducials or markers in order to enter or initialize position coordinates in a tracking system that operates by triangulating paths, angles or distances to various signal emitting or reflecting markers. A hybrid tracking system may also be used, including one or more robotic elements which physically encode mechanical positions of linkages or supports as part of one or more of the tracking measurements being made. Preferably, however, the tracking system employs electromagnetic tracking elements such as shown in U.S. Pat. No. 5,967,980, to generate and/or detect electromagnetic field components that pass through or are substantially unobstructed by the patient and intervening structures, and to directly determine coordinates in three or more dimensions referenced to the tool, the patient or the fluoroscope to which the elements are attached.

A single tracking element may be affixed to each of the fluoroscope, the patient, and the surgical tool. One presently preferred embodiment of a tracking element employs a magnetic field element, such as one configured with three mutually orthogonal coils, that otherwise operates as a substantially point-origin field generator or field sensor. The element may have a rigid or oriented housing, so that when attached to a rigid object, the tracked coordinates of the element yield all coordinates, with only a defined constant offset, of the object itself. The element may be energized as a field generator, or sampled as a field sensor, to produce or detect a field modulated in phase, frequency or time so that some or all of the x-, y-, z-, roll-, pitch-, and yaw coordinates of each tracking element, and thus its associated object, are quickly and accurately determined. A table of position correction factors or characteristics may be compiled for one or more of the tracking elements to correct for the effects of electromagnetic shunting or other forms of interference with the generator or receiver which may occur when positioned in a region near to the body of the fluoroscope. This allows a magnetic tracking element to be placed quite close to the imaging assembly or other conductive structure and achieve high position tracking accuracy or resolution. In particular, one or more tracking elements may be mounted directly on the fluoroscope and/or on calibration fixtures positioned close to the image detector of the fluoroscope to define camera and imaging parameters relative to another tracker which may move with the patient or with a tool. Various alternative magnetic generating and sensing assemblies may be used for the tracking component, such as ones having a tetrahedrally-disposed generating element and a single sensing/receiving coil, or ones having a multipole generating assembly that defines a suitably detectable spatial field.

BRIEF DESCRIPTION OF THE DRAWINGS

The invention will be understood from the description and claims herein, viewed in light of the prior art, and taken together with the Figures illustrating several basic embodiments and representative details of construction, wherein

FIG. 3 shows details of one camera calibration subassembly useful in the embodiment of FIG. 1;

DETAILED DESCRIPTION OF THE INVENTION

Figure 1:
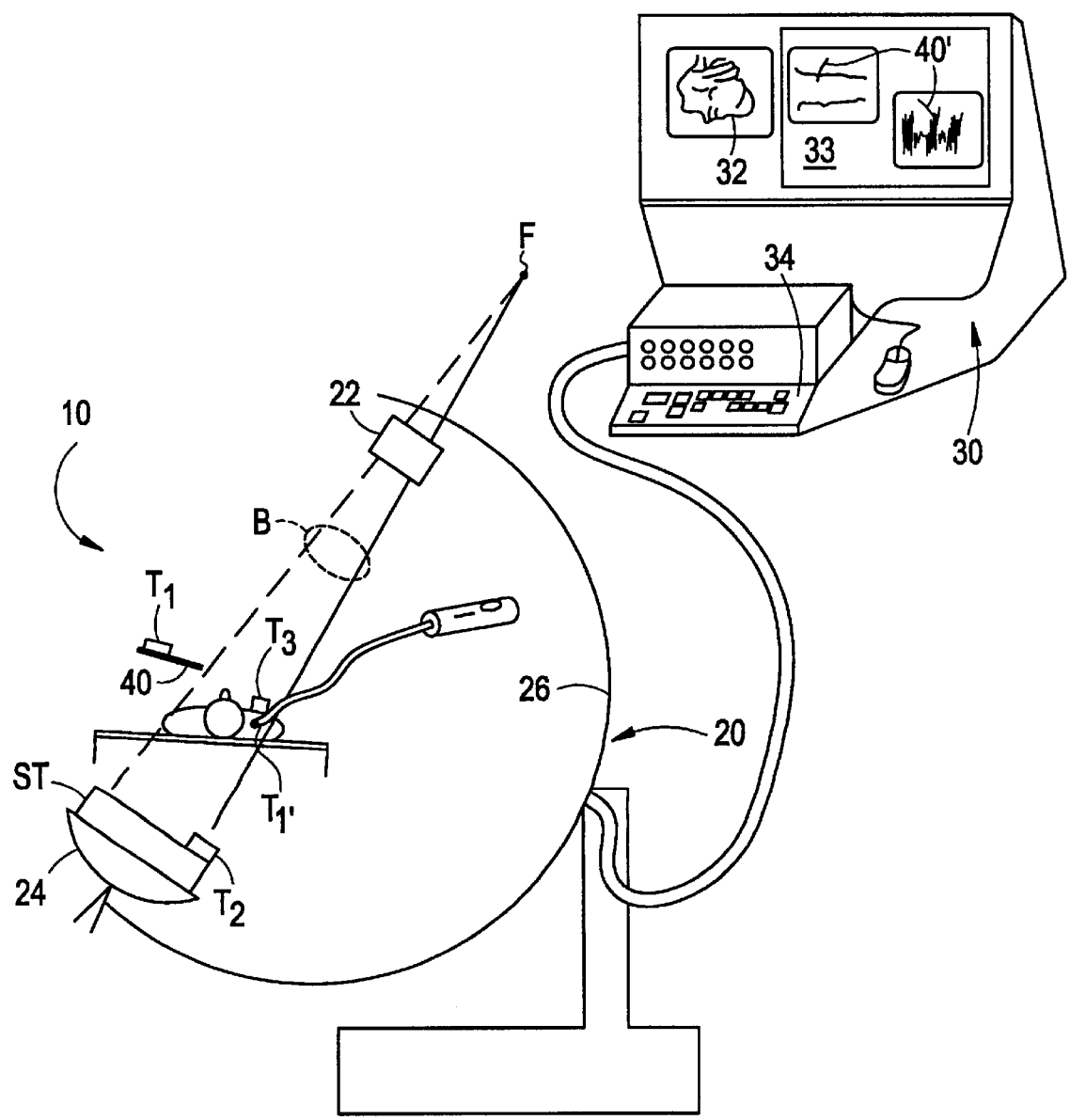
FIG. 1 illustrates a fluoroscopic image and tool navigation system in accordance with one embodiment of the present invention.

FIG. 1 illustrates elements of a basic embodiment of a system 10 in accordance with the present invention for use in an operating room environment. As shown, the system 10 includes a fluoroscope 20, a work station 30 having one or more displays 32 and a keyboard/mouse or other user interface 34, and a plurality of tracking elements T1, T2, T3. The fluoroscope 20 is illustrated as a C-arm fluoroscope in which an x-ray source 22 is mounted on a structural member or C-arm 26 opposite to an x-ray receiving and detecting unit, referred to herein as an imaging assembly 24. The C-arm moves about a patient for producing two dimensional projection images of the patient from different angles The patient remains positioned between the source and the camera, and may, for example, be situated on a table or other support, although the patient may move. The tracking elements, described further below, are mounted such that one element T1 is affixed to, incorporated in or otherwise secured against movement with respect to a surgical tool or probe 40. A second tracking unit T2 is fixed on or in relation to the fluoroscope 20, and a third tracking unit T3 fixed on or in relation to the patient. The surgical tool may be a rigid probe as shown in FIG. 1, allowing the tracker T1 to be fixed at any known or convenient position, such as on its handle, or the tool may be a flexible tool, such as a catheter, flexible endoscope or an articulated tool. In the latter cases, the tracker T1 is preferably a small, localized element positioned in or at the operative tip of the tool as shown by catheter tracker T1' in FIG. 1, to track coordinates of the tip within the body of the patient.

As will be understood by those skilled in the art, fluoroscopes typically operate with an x-ray source 22 positioned opposite the camera or image sensing assembly 24. While in some systems, the X-ray source is fixed overhead, and the camera is located below a patient support, the discussion below will be illustrated with regard to the more complex case of a typical C-arm fluoroscope, in which the source and camera are connected by a structural member, the C-arm, that allows movement of the source and camera assembly about the patient so it may be positioned to produce x-ray views from different angles or perspectives. In these devices, the imaging beam generally diverges at an angle, the relative locations and orientations of the source and camera vary with position due to structural flexing and mechanical looseness, and the position of both the source and the camera with respect to the patient and/or a tool which it is desired to track may also vary in different shots.

The imaging beam illustrated by B in FIG. 1 diverges from the source 22 in a generally truncated conical beam shape, and the C-arm 26 is movable along a generally arcuate path to position the source and camera for imaging from different directions. This generally involves positioning the camera assembly 24 as close as possible behind the relevant tissue or operating area of the patient, while the C-arm assembly is moved roughly about a targeted imaging center to the desired viewing angle. The C-arm or other beam structure 26 may be a somewhat flexible structure, subject to bending, deflection or sagging as the source and camera move to different positions around the patient, and the C-arm may also have other forms of dimensional variation or looseness, such as drive gear backlash, compressible elastomeric suspension components or the like, which may contribute to variations and non-repeatability of the relative disposition and alignment of the source and camera with respect to each other, and with respect to the patient, as the assembly is moved to different positions. The C-arm may also move eccentrically or translationally to allow better clearance of the patient support table. The bending deflections of the C-arm assembly may vary the actual position of the source 22 by almost a centimeter or more with respect to the image detector, and displace it from a nominal position which may be indicated, for example, by an encoder present in the fluoroscope stand or C-arm positioning assembly. These variations may therefore be significant.

Figure 1A:
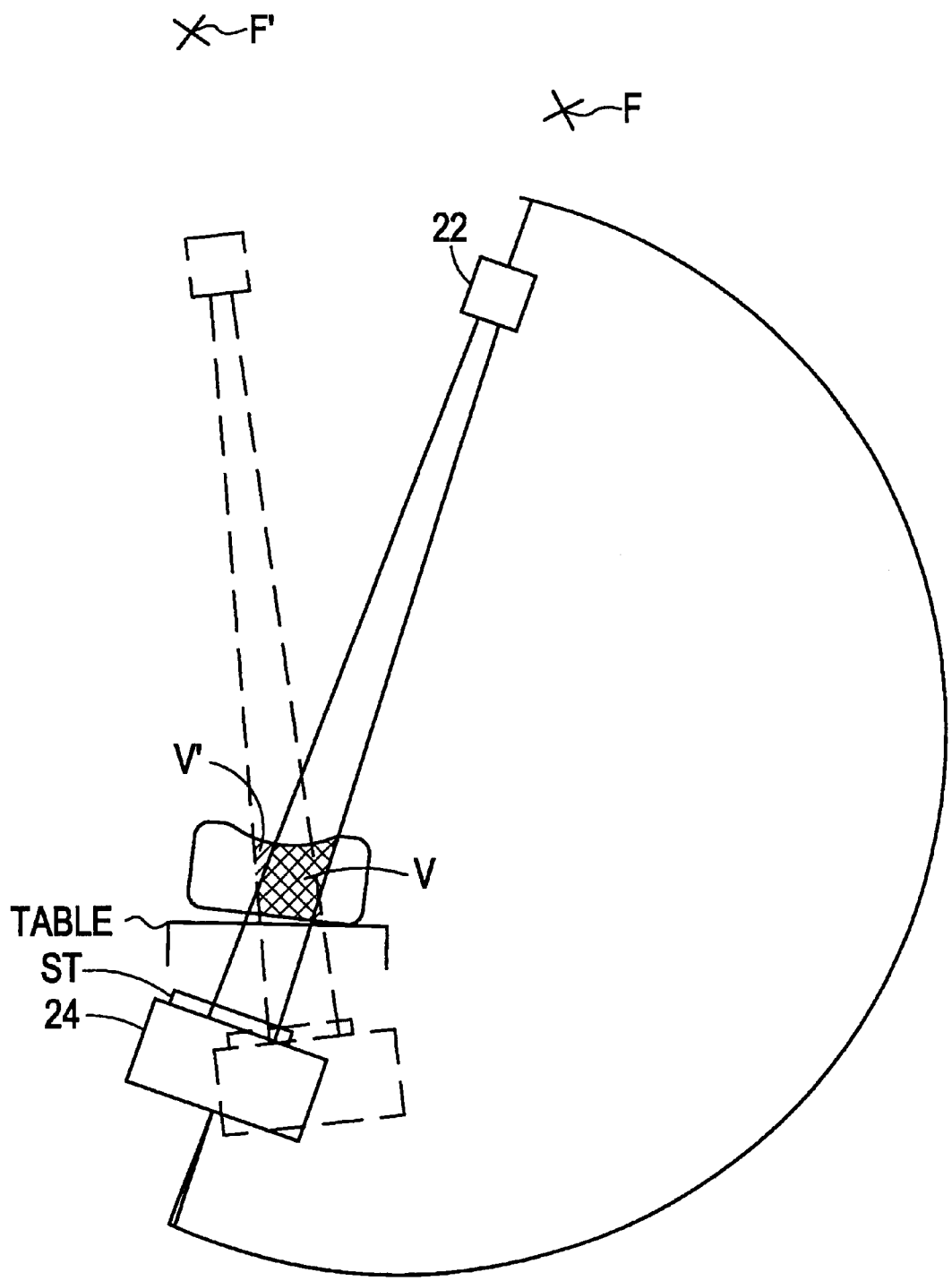
FIG. 1A illustrates camera imaging of a tissue region with the system of FIG. 1.

FIG. 1A illustrates the fluoroscope 20 in two different imaging positions, with a first position shown in solid line, and a second position in dashed line phantom. In the first position, a tissue volume V is imaged with a divergent beam from the above right, and a virtual beam origin or focal point at F, while the image from the second position catches a largely overlapping but partly distinct tissue volume with a divergent beam from the upper left, and a different focal point F'. The distances from points F, F' to the camera may be different, and the camera itself may shift and tilt with respect to the beam and its center axis, respectively. In practice, the x-ray beam is generally aimed by its center ray, whose intersection with the imaging plane, referred to as the piercing point, may be visually estimated by aiming the assembly with a laser pointing beam affixed to the source. The x-ray beam may be considered to have a virtual origin or focal point F at the apex of the cone beam. Generally, the camera assembly 24 is positioned close to the patient, but is subject to constraints posed by the operating table, the nature of the surgical approach, and the necessary tools, staging, clamps and the like, so that imaging of a tissue volume somewhat off the beam center line, and at different distances along the beam, may occur. As noted above, flexing of the C-arm also changes the distance to the focal point F and this also may slightly vary the angular disposition of the beam to the camera, so this shifting geometry may affect the fluoroscope images.

Furthermore, the camera 24 may utilize an image sensing unit that itself introduces further distortions into the received distribution of image radiation. For example, the unit may involve a detector that employs a phosphor surface of generally curved contour to convert the x-ray image intensity distribution to a free electron distribution. Such a curved phosphor screen is generally placed over an electron multiplier or image intensifier assembly that provides an enhanced output video signal, but may further introduce a form of electron optical distortion that depends upon the intensifier geometry and varies with the orientation of the camera assembly in the earth's magnetic field. Other configurations of image detectors are also known or proposed, such as digital x-ray detectors or flat semiconductor arrays, which may have different imaging-end fidelity characteristics. In any case, deflection or physical movement of the camera itself as well as electron/optical distortion from the camera geometry, image detector and variations due to gravitational, magnetic or electromagnetic fields can all enter the image reception and affect the projective geometry and other distortion of the final image produced by the assembly.

The foregoing aspects of imaging system variability are addressed by the present invention by using tracking elements in conjunction with a camera calibration fixture or correction assembly to provide fluoroscopic images of enhanced accuracy for tool navigation and workstation display.

A more detailed description of the operation of the present invention follows, and proceeds initially from 1) a mechanism for effectively characterizing camera imaging parameters while addressing distortion in each image frame or shot of a C-arm fluoroscope to 2) using these parameters to reconstructing a 3D volume that is dynamically referenced to the patient and the tool; and finally 3) fusing the dynamically referenced 3D volume with preoperative volumetric data. The equipment and procedure has two components, a first component provided by a tracking assembly which determines position of a fluoroscope calibration fixture relative to one or both of the tool and patient body, and a second component provided by a processor operating on each image that characterizes or models the geometry of the camera and performs all subsequent processing. This is done by providing a calibration fixture that contains an array of markers, which is either tracked as a rigid unit or affixed to the camera, while the imaged position of the markers in each fluoroscope shot serves to characterize the imaging geometry so as to allow correction of imaged features at measured distances from the camera, and permit registration of successive images in different poses.

Figure 2:
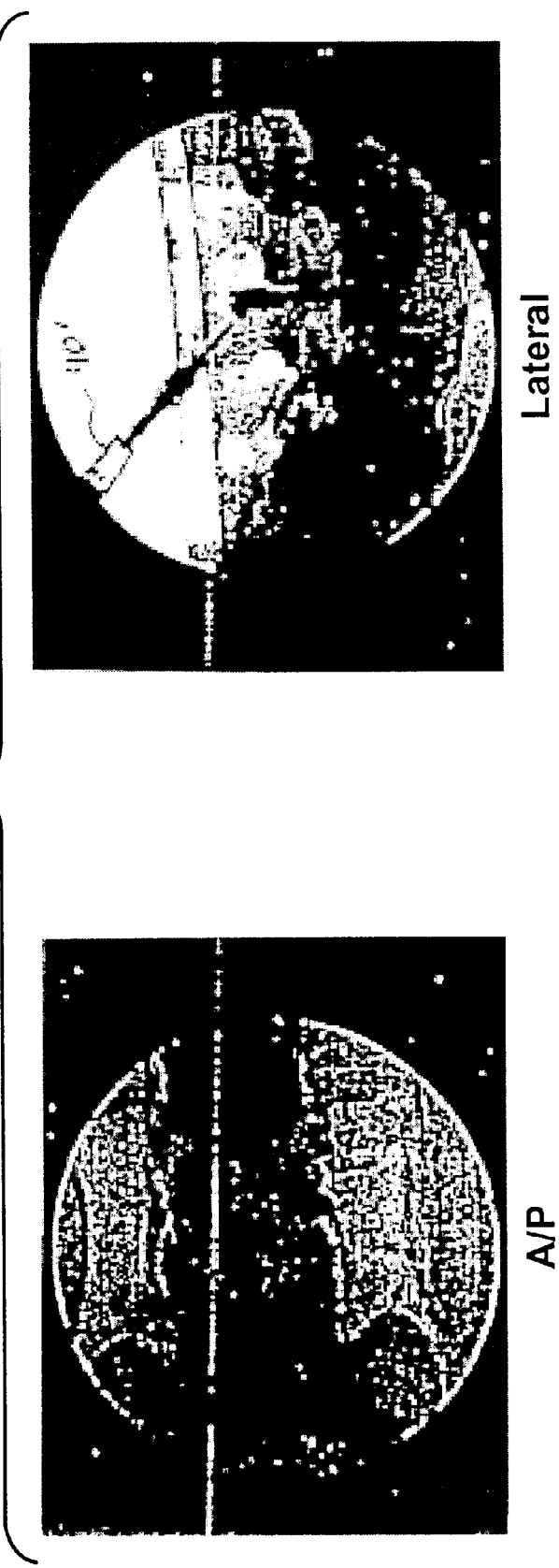
FIG. 2 illustrate representative navigation images of one embodiment of the system of FIG. 1.

In accordance with a principal aspect of the present invention, when tracked relative to a tool, the surgical instrument display 40' of FIGS. 1 and 2 is effected by determining tool position, focus and imaging axis, and rendering the instrument in conjunction with one or more of the three types of images mentioned above. In one embodiment, the processor determines an image distortion inverse transform and projects a distorted or transformed tool graphic or image on the fluoroscopic view. In another aspect, the processor determines the camera geometry for each image and transforms the set of fluoroscopic images such that the screen coordinates of display 33 are similar or aligned with the operating coordinates as measured by tracking elements T2, T3. This calibration results in more accurate tool tracking and representation over time. As further discussed in regard to FIG. 5 below, the image data of an imaging sequence for a region of tissue about a common origin may be back-projected or otherwise processed to define a three dimensional stack of fluoro-CT images. The invention thus allows a relatively inexpensive C-arm fluoroscope to achieve accuracy and registration to prepare CT images for tool guidance and reconstruction of arbitrary planes in the imaged volume.

In overall appearance, the data processing and work station unit 30 illustrated in FIG. 1 may be laid out in a conventional fashion, with a display section in which, for example, a previously acquired CT or diagnostic image is displayed on one screen 32 while one or more intraoperative images 33, such as a A/P and a lateral fluoroscopic view, are displayed on another screen. FIG. 2 schematically represents one such display. In its broad aspects the system may present an appearance common to many systems of the prior art, but, in a first aspect provides enhanced or corrected navigation guiding images, while in a second aspect may provide CT or other reconstructed images in display 32 formed directly from the fluoroscopic views. In a third aspect the system may provide dynamic referencing between these reconstructed images and a set of preoperative 3D image data.

Figure 2A:
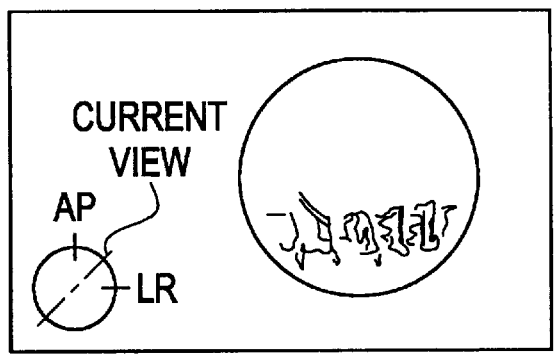
FIG. 2A illustrates the display of fluoroscope orientation in a preferred implementation of the system of FIG. 1.

Typically, for tool positioning, one fluoroscope image in display 33 may be taken with the beam disposed vertically to produce an A/P fluoroscopic image projected against a horizontal plane, while another may be taken with beam projected horizontally to take a lateral view projected in a vertical plane. As schematically illustrated therein, the image typically shows a plurality of differently shaded features, so that a patient's vertebra, for example, may appear as an irregular three-dimensional darkened region shadow-profiled in each of the views. The tool representation for a navigation system may consist of a brightly-colored dot representing tip position and a line or vector showing orientation of the body of the tool approaching its tip. In the example shown in FIG. 2, in the horizontal plane, the probe projected image 40' may extend directly over the imaged structure from the side in the A/P or top view, while when viewed in the vertical plane the perspective clearly reveals that the tip has not reached that feature but lies situated above it in space. In a preferred implementation of the multi-image display console of the invention, the display employs position data from the tracking assembly to display the fluoroscope's current angle of offset from the baseline AP and lateral views. Surgeons have generally become accustomed to operating with such images, and despite the fact that the fluoroscopic images are limited by being projection images rather than 3D images, their display of approximate position and orientation, in conjunction with the diagnostic image on panel 32 which may also have a tool point representation on it, enables the surgeon to navigate during the course of a procedure. In a preferred embodiment of the present invention, this display is further enhanced by employing position data from the tracking assembly to display the fluoroscope's current angle of offset from the baseline AP and lateral fluoroscope views. This may be done as shown in FIG. 2A, by marking the fluoroscope's tracked angle or viewing axis with a marker on a circle between the twelve o'clock and three o'clock positions representing the AP and lateral view orientations.

The nature of the enhancement or correction is best understood from a discussion of one simple embodiment of the present invention, wherein a tracking system tracks the surgical instrument 40, and the system projects a representation 40' of the tool on each of the images detected by the image detector 24. This representation, while appearing as a simple vector drawing of the tool, is displayed with its position and orientation determined in the processor by applying a projective transform and an inverting image distortion transformation to the actual tool coordinates determined by the tracking elements. Thus, it is displayed in "fluoroscope image space", rather than displaying a simple tool glyph, or correcting the image to fit the operating room coordinates of the tool.

FIG. 3 illustrates one embodiment 50 of a suitable marker array, calibration fixture or standard ST for the practice of the invention. As illustrated in this prototype embodiment, the fixture may include several sheets 52 of radiolucent material, each holding an array of radiopaque point-like markers 54, such as stainless steel balls. (hereafter simply referred to as BBs). The BBs may be of different sizes in the different planes, or may be of the same size. Preferably, they are of the same size, e.g., about one or two millimeters in diameter, and preferably the one or more plates holding them are rigidly affixed at or near to the face of the camera imaging assembly so as to allow accurate calibration of the entire volume of interest while occupying a sufficiently small space that the camera may be positioned closely to the patient. The illustrated calibration fixture 50 includes a releaseable clamp assembly 51, with a camming clamp handle 51a, configured to attach directly on or over the face of the camera assembly.

As shown in the system diagram, FIG. 4, operation of the system proceeds as follows.

Initially, as noted above, a tracking element is associated with each of the tool, the patient and the fluoroscope. Each tracking element is secured against movement with respect to the structure it is tracking, but advantageously, all three of those structures are free to move. Thus, the fluoroscope may move freely about the patient, and both the patient and the tool may move within the operative field. Preferably, the tracking element associated with the fluoroscope is positioned on a calibration fixture 50 which is itself rigidly affixed to the camera of the fluoroscope as described above. The calibration fixture may be removably attached in a precise position, and the tracking element T2 may be held in a rigid oriented body affixed to the fixture 50. The tracking element T2 (FIG. 3) may, for example, be a point-origin defining tracking element that identifies the spatial coordinates and orientation of its housing, hence, with a rigid coordinate transform, also specifies the position and orientation coordinates of the object to which it is attached. Thus, the tracking element T2 may with one measurement determine the positions of all markers in the calibration fixture, and the position and orientation of the fixture itself or the horizontal surface of the camera assembly.

Figure 3A:
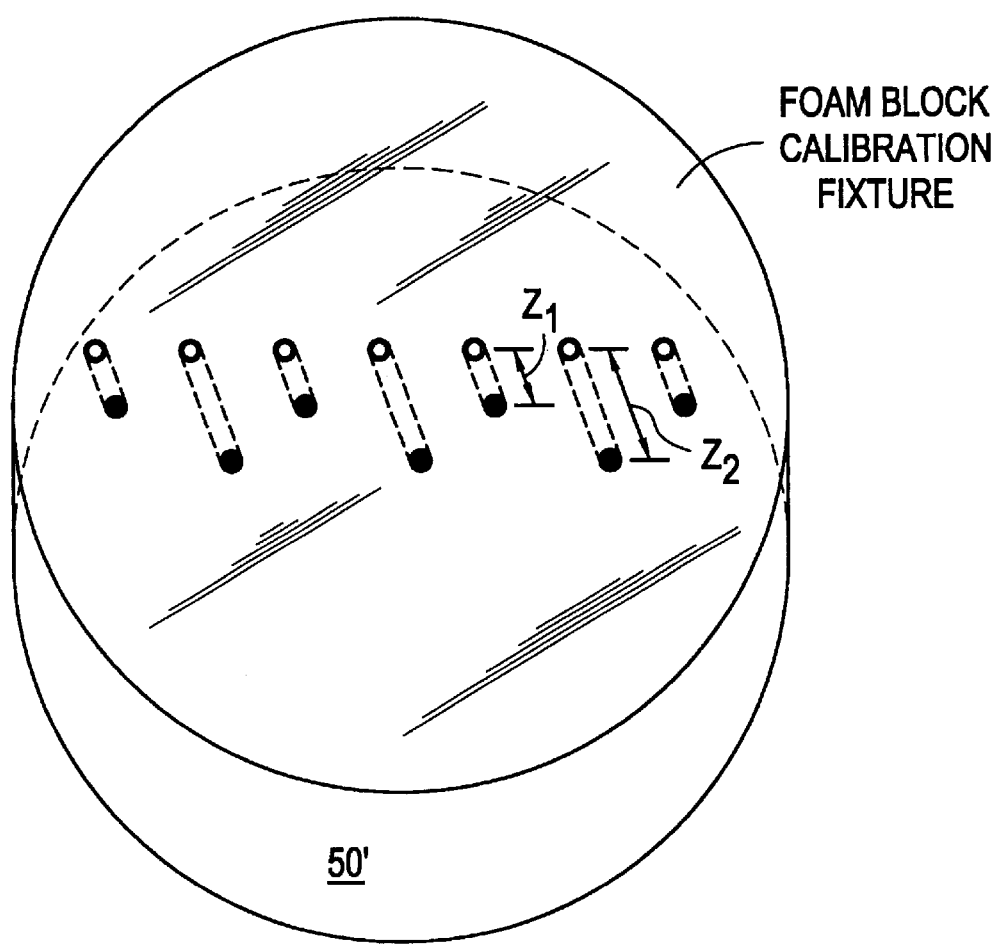
FIG. 3A shows another calibration sub-assembly of the invention.

The illustrated marker plates may each be manufactured by NC drilling of an array of holes in an acrylic, e.g., Lexan, and/or other polymer plate, with the BBs pressed into the holes, so that all marker coordinates are exactly known. Alternatively, marker plates may be manufactured by circuit board microlithography techniques, to provide desired patterns of radiopaque markers, for example as metallization patterns, on one or more thin radiolucent films or sheets. Applicants also contemplate that the calibration assembly, rather than employing separate sheets bearing the markers, may be fabricated as a single block 50 of a suitable radiolucent material, such as a structural foam polymer having a low density and high stiffness and strength. In that case, as shown in FIG. 3A, holes may be drilled to different depths and BB markers may be pressed in to defined depths $Z_1$, $Z_2$ . . . at specific locations to create the desired space array of markers in a solid foam calibration block. One suitable material of this type is a structural foam of the type used in aircraft wings for lightweight structural rigidity. This material may also be employed in separate thin marker-holding sheets. In any case the selected polymer or foam, and the number and size of the markers, are configured to remain directly in the imaging beam of the fluoroscope device and be imaged in each shot, while the position of the fixture is tracked. The fixture materials are selected to avoid introducing any significant level of x-ray absorption or x-ray scattering by the plates, sheets or block, and the size and number of markers are similarly chosen to avoid excessive shadowing of the overall image, while maintaining a sufficiently dense image level for their detectability, so that both the imaging source radiation level and the resulting image density scale remain comparable to currently desired operating levels. Preferably, the BBs are arranged in a pattern at one or more levels, with a different pattern at each level. Further, when more than one array at different depths is used, the patterns are positioned so that as the source/camera alignment changes, BBs of one pattern cast shadows substantially distinct from those of the other pattern(s).

As noted above, in accordance with a principal aspect of the present invention, the array of markers is imaged in each fluoroscope shot. As shown in FIG. 4, the image display system of the present invention operates by first identifying markers in the image. This is done in an automated procedure, for example, by a pipeline of grey level thresholding based on the x-ray absorption properties of the markers, followed by spatial clustering based on the shape and size of the markers. In the preferred embodiment having two or more planar sheets, each sheet has markers arranged in a particular pattern. The pattern of each sheet will be enlarged in the image by a scale that varies with the cone divergence and the distance of the marker sheet along the axis from the optical center (or x-ray source) to the detection surface. The marker images will also be shifted radially away from the beam center axis due to the beam divergence. In the preferred embodiment, the calibration fixture is positioned close to the image detection surface, and the markers lie in arrays distributed in planes placed substantially perpendicular to the optical axis and offset from the detection surface. In general, not all markers will be located in the image due to shadowing of some of markers, or occlusion of the marker by another object of similar x-ray absorption response. In a prototype embodiment of the marker identification image processor, the candidate markers in the image are first identified using image processing and then matched with corresponding markers in the fixture.

One suitable protocol takes a candidate marker $P_i$ in image coordinates, assumes it is, e.g., marker number $Q_j$ of sheet one, and then determines how many other candidate markers support this match, i.e., line up with the expected projections of the remaining markers of one array, e.g., in the pattern of sheet one. The number of candidates matching the known template or pattern of sheet one is totaled, and is taken as the score of that marker. This process is repeated to score each candidate marker in the image, and an identification scored above a threshold is taken as correct when it leads to the highest score for that candidate, and does not conflict with the identification of another high-scoring candidate. Scoring of the match is done by using the observation that the ratio of distances and angles between line segments on the same plane are invariant under perspective projection. When the array has only about fifty to one hundred markers, the processor may proceed on a point-by-point basis, that is, an exhaustive matching process may be used to determine the correspondence between points. When a larger number of markers are desired, the marker detection processor preferably employs an optimization algorithm such as the Powell, Fletcher or a simplex algorithm. One particularly useful pattern matching algorithm is that published by Chang et al in Pattern Recognition, Volume 30, No. 2, pp. 311–320, 1997. That algorithm is both fast and robust with respect to typically encountered fluoroscopic distortions. As applied to calibration markers of the present invention, the Chang alignment/identification algorithm may be accelerated relying upon the fact that the marker fixture itself has a known marker geometry. For example, the marker identification module may predict the expected positions in the image, and search for matches within a defined small neighborhood. The image processor calibration module includes a pre-compiled table, for example, stored in non-volatile memory, indicating the coordinates of each marker of the pattern, and preferably includes tables of separation for each pair, and/or included angle for each triplet of markers, to implement fast identification.

As noted above, when the calibration plates are rigidly affixed to the camera, only a single tracking element T2 is needed to determine the positions of all the markers, which differ only by a rigid transform (e.g. a translation plus a rotation) from those of the tracking element. Otherwise, if one or more of the arrays of markers is carried in a separately-positioned sheet or fixture, each such unit may be tracked by a separate tracking element. In either case, the array of marker positions are determined in each fluoroscopic image frame from the tracking element T2 and from the fixed relative position coordinates stored in the marker table.

Figure 4:
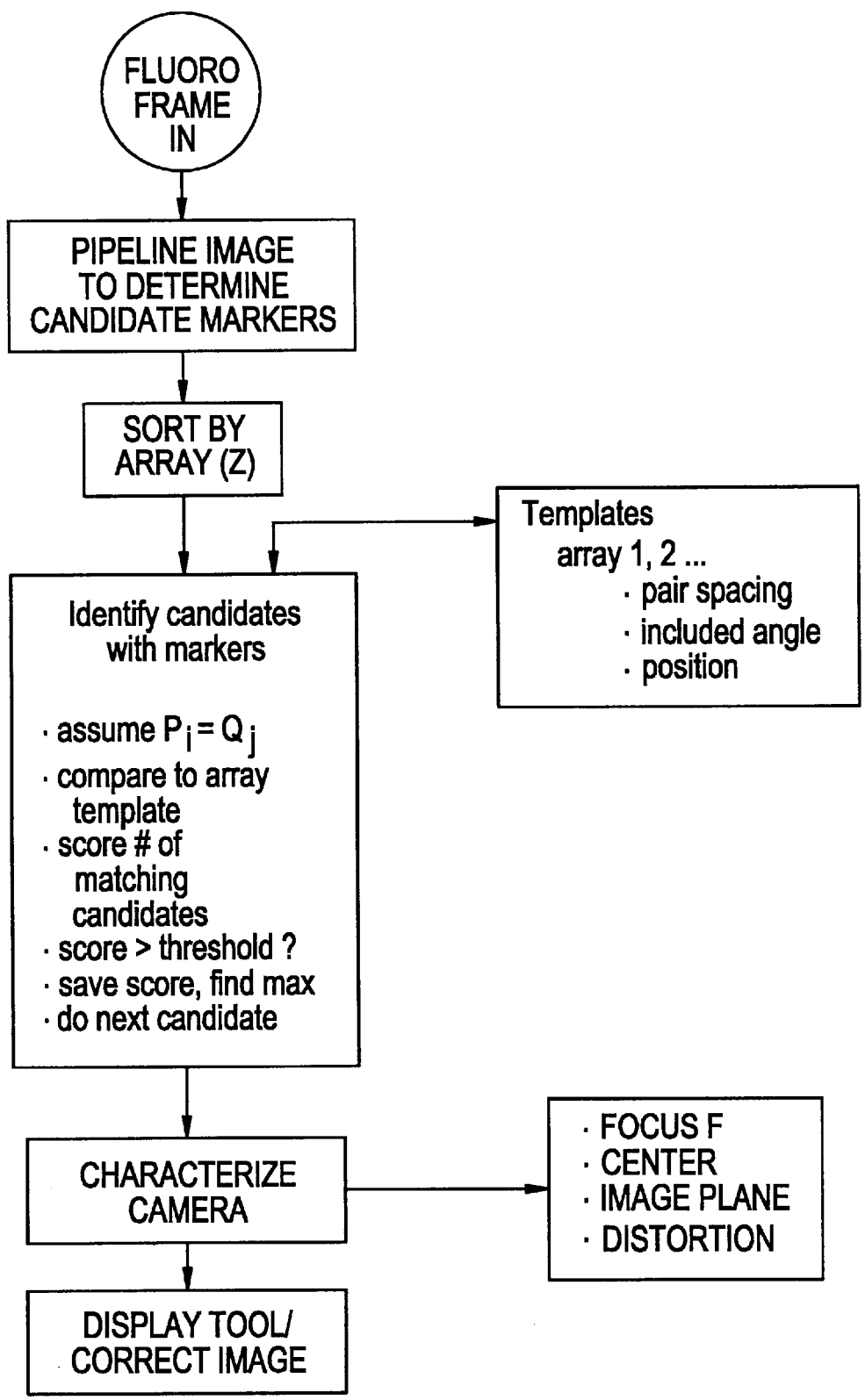
FIG. 4 is a flow chart showing image processing and tool tracking in accordance with a first aspect of the invention.

Continuing with a description of FIG. 4, in accordance with a principal aspect of the invention, the camera is next calibrated using the marker identification information of the previous steps. The imaging carried out by the fluoroscope is modeled as a camera system in which the optical center is located at the x-ray source and the imaging plane is located a distance F (focal length) away from it inside the camera assembly. The optical axis is the line through the x-ray source and perpendicular to the horizontal face of the camera. The intersection of the optical axis and the image plane is defined as the piercing point. Certain imaging or distortion characteristics may also be measured by the array of marker images, which thus determines a corrective perspective transformation. A suitable algorithm is that described by Roger Tsai in his article on 3-D camera calibration published in the *IEEE Journal of Robotics and Automation,* Volume RA-3, No. 4, August 1987, pp. 323–344. This model determines radial distortion in addition to parameters using an algorithm that takes as input the matched marker and image locations, estimates of focal length and information about the number of rows and columns in the projection image. This algorithm is readily implemented with one or more planes of markers in the fixture 50 or 50'. When the fluoroscope is sufficiently rigid that focus does not vary, a single plane of markers may be used to define the camera parameters.

By providing a pattern of markers in a plane, the shifts in position of those markers in the image define a local transformation that corrects for radial distortion of the image, while non-occluding markers in two planes, or at two different positions along the z-axis are sufficient to identify the focus and the optical or center axis of the beam. Other models relying, for example, on defining a distortion morphing transformation from the array of marker images may also be applied. A pattern of markers may comprise a rectangular lattice, e.g., one marker every centimeter or half-centimeter in two orthogonal directions, or may occupy a non-periodic but known set of closely-spaced positions. The calibration fixture may be constructed such that markers fill a peripheral band around the imaged tissue, to provide marker shadow images that lie outside the imaged area and do not obscure the tissue which is being imaged for display. Preferably, however, the markers are located in the imaged field, so that the imaging camera and distortion transforms they define closely fit and characterize the geometric imaging occurring in that area. In the preferred embodiment, the image processor removes the marker shadow-images from the fluoroscope image frame before display on the console 30 (FIG. 1), and may interpolate or otherwise correct image values in the surrounding image.

Continuing with a description of the processing, the processor in one basic embodiment then integrates tracked tool position with the fluoroscope shot. That is, having tracked the position of tool 40 via tracking element $T_1$, relative to the marker array 50 and tracking element $T_2$, and having modeled the camera focus, optical axis and image plane relative to the position of the fixture 50, the system then synthesizes a projection image of the tool as it dynamically tracks movement of the tool, and displays that tool navigation image on the fluoro A/P and/or lateral view of screen 33 (FIG. 1).

To display the tool position on an uncorrected fluoroscope image, the processor obtains the position of the front and back tips of the tool. These are fixed offsets from the coordinates of the tracking element T1 associated with the tool. The tracker may also determine tool orientation relative to the patient from position and orientation relative to the tracking element T3 on the patient at the time of image capture. Tracked position coordinates are converted to be relative to the fixed tracking element on the camera, or so that all coordinates reference the image to which the camera model applies. In a basic tool navigation embodiment, the camera calibration matrix is then applied to the front and back tip position coordinates of the tool to convert them to fluoroscope image space coordinates. These end point coordinates are converted to undistorted two-dimensional image coordinates (e.g., perspective coordinates) using the calculated focal length of the camera, which are then converted to distorted two-dimensional image coordinates using the lens distortion factor derived from the matrix of marker positions. Corresponding pixel locations in the two-dimensional fluoroscope image are determined using the x-scale factor, the calculated origin of the image plane and scaling based on the number of pixels per millimeter in the camera image sensor and display. The determined position is then integrated with the video display on the fluoroscope to show a graphical representation of the tool with its front tip location in image coordinates. Preferably, the tool is displayed as an instrument vector, a two-dimensional line on the fluoroscopic image with a red dot representing its tip. Thereafter, during an ongoing procedure, the tracking assembly may track tool movement relative to the patient, and a processor controls the tracking and determines from the position of the tool when it is necessary to redraw the integrated display using the above-described image distortion transformations to correctly situate the displayed tool in a position on a new image.

As described above, the process of camera calibration is a process of applying actual coordinates as determined by the tracking system and marker positions, and image coordinates as seen in the fluoroscopic marker images, to model a camera for the image. In general, applicant's provision of an array of marker points having known coordinates in each of several planes, together with tracking coordinates corresponding to the absolute position of those planes and modeling of the camera image plane with respect to these tracked positions obviates the need for lengthy initialization or correlation steps, and allows an image processor to simply identify the marker images and their positions in the image, model the camera to define focus, image plane and piercing point, and to effect image corrections with a few automated tracking measurements and transformations. The fixture is preferably fixed close to the front surface of the image detector assembly, so the calibration fits the detected image closely.

As noted above, the marker positions allow a simple computation of effective parameters to fully characterize the camera. This allows one to scale and correct positions of the image (for example a tool) when their coordinates are tracked or otherwise unknown.

In accordance with a preferred method of operation of the present device, the fluoroscope is operated to take a large number of fluoro images, with fixture tracking and camera modeling as described above, and a 3D CT image data set is reconstructed from the acquired data. In general, this data set can be acquired such that it is dimensionally accurate and useful for close surgical guidance, although parameters such as x-ray absorbance, corresponding, for example to bone or tissue density, will be of lesser accuracy than those obtainable from a CT scanner, and should not be relied upon. The fluoroscopic CT images so formed may be further correlated with preoperative MRI, PET or CT images to define a direct image coordinate transformation, using established techniques such as MI (mutual information) registration, edge or contour matching, or the like, between the fluoroscopic 3D data set of the present invention and the existing preoperative 3D image set.

Operation for forming a volume image data set for CT reconstruction proceeds as follows. First, the fluoroscope is operated to obtain a dense set of fluoroscope images, for example, by rotating the fluoroscope approximately in a plane about the patient through 180° plus the angle of divergence of the cone beam, taking a shot every degree or less, so as to image a particular three-dimensional tissue volume of the patient in a large number of images. As each frame is acquired, pose information, given for example by the position and orientation measurement of the tracking element T2, is stored, and the marker detection/calibration module operates on each shot so that a correction factor and a perspective projection matrix is determined for each image, as described above, to model the camera focus, image plane and optical axis for that shot. A coordinate system for the tissue volume for which reconstruction is desired is then computed, and the processor then applies filtered back projection or other reconstruction processing (such as lumigraphs or lambda-CT), with indexing provided by the relative disposition of each pose, to reconstruct a three-dimensional volume data image set in the intraoperative coordinate system for a region of tissue around the origin of the reconstruction coordinate system. This 3-D image data set referenced to tracker coordinates readily allows CT reconstruction of desired planes within the image set, referenced to patient or tool position.

In order to integrate the tracking system with the fluoroscopic images, it is necessary to establish a coordinate system for the three-dimensional reconstructed volume. This entails defining the origin and the coordinate axes for that volume. Once such a coordinate system is defined in relation to all fluoro images, one can compute the back projection at voxels in a region referenced to the origin, in planes that are perpendicular to one of the coordinate axes. In the case of a spinal scan, for example, the desired CT planes will be planes perpendicular to an axis that approximates the long axis of the body. Such a spinal data set is especially useful, since this view cannot be directly imaged by a fluoroscope, and it is a view that is critical for visually assessing alignment of pedicle screws. Applicant establishes this common coordinate system in a way that minimizes risk of: (a) backprojecting voxels where insufficient data exists in the projections or (b) being unable to define the relationship between the natural coordinate system of the patient and that of the reconstruction.

In the discussion that follows, it will be assumed that the user, e.g., the surgeon, or radiologist takes the fluoroscopic images such that the region of interest stays visible, preferably centered, in all the fluoroscopic images and that each arc traced by the C-arm is approximately planar. These requirements may be met in practice by users of C-arm fluoroscopes, since surgeons have extensive practice in acquiring fluoroscopic images by tracing planar motion trajectories in which the relevant anatomy is centered in both AP and lateral views. Such centering is easiest to achieve, or most accurately attained when using a substantially isocentric C-arm such as that made by the Siemens corporation. However, in calibrating the camera for each image, applicants are able to automatically determine a reconstruction coordinate system for an arbitrary sequence of images. In this regard, the camera tracking data may be used to fit a center. This is considered an advance over systems that require a coordinate system to be specified manually.

It will be appreciated that in the above-described system, the tracking elements automatically detect coordinates of the marker array, tool and patient at the time each image is taken. Detection of the calibration fixture position allows camera modeling to provide the position of the optical center (F), optical axis and image plane, in tracker coordinates for each shot as described above. In accordance with this further aspect of the invention, the combination of tracked position and modeled camera information is used to define a coordinate system for the reconstruction, which is preferably computed by performing statistical and computational geometry analysis on the pose information recorded and derived for each of the fluoroscopic image frames.

A few definitions will clarify the underlying procedure, employed in the prototype embodiment and automated in software. The "projection plane" is the plane on which the image is formed through the operation of perspective projection. The "optical center" or the "center of projection", C, is located at a distance F, the focal length of the optical system, from the projection plane. In the case of a fluoroscope, this is the actual location of the x-ray source; the source is positioned at the optical center of the imaging system. The projection of a given point M in the world is computed as the intersection of the ray connecting M and the optical center C with the projection plane. The "optical axis" of a fluoroscopic imaging system is the line that passes through its optical center (the x-ray source) and is normal to the projection plane. The point at which the optical axis intersects the projection plane is known as the "principal point" or the "piercing point". A textbook such as "Three-Dimensional Computer Vision" by Olivier Faugeras, MIT Press, may be consulted for further background or illustration of basic concepts used here.

Figure 5:
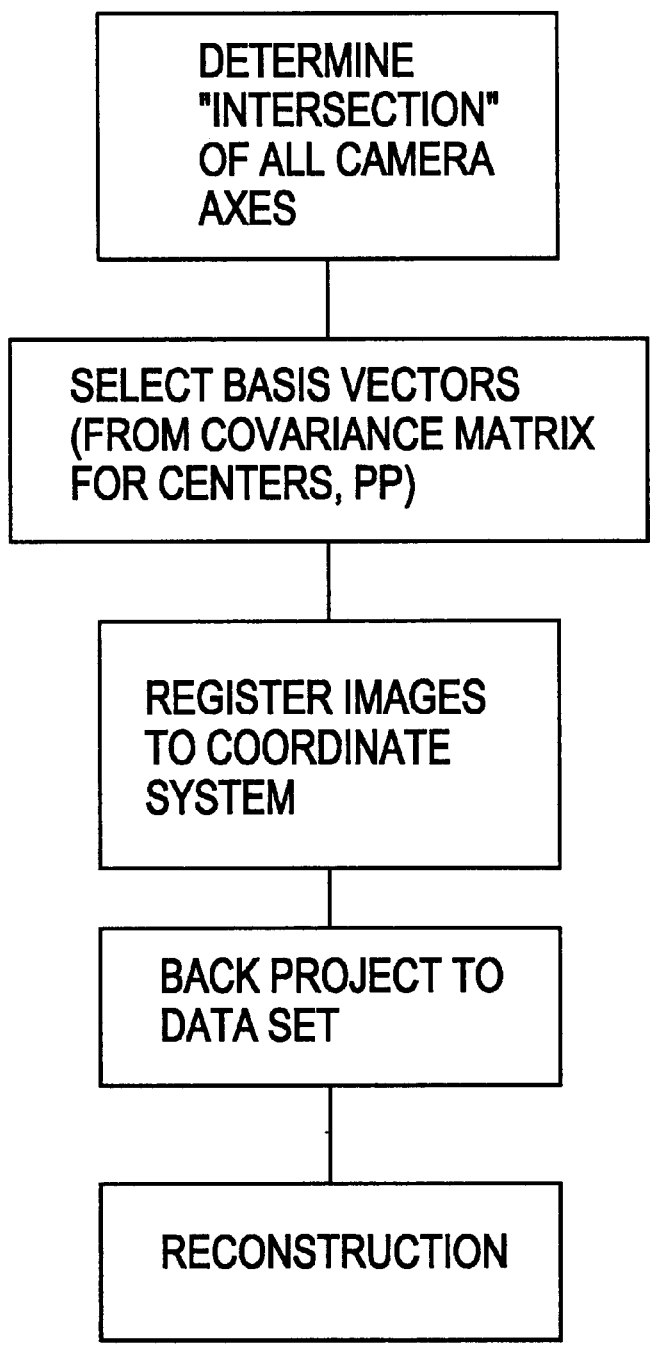
FIG. 5 illustrates operation of a second aspect of the invention.

Applicant's approach to the problem of computing a coordinate origin for reconstruction assures that in this set of data, the origin of the 3D coordinate system lies at a point that is the center of the region that the surgeon is most interested in visualizing. That point is identified in a prototype system by computing a point that is closest to being centered in all of the acquired fluoroscopic images, and then taking that point as the origin of a coordinate system in which the reconstruction is performed. FIG. 5 sets forth the steps of this processing.

Figure 7:
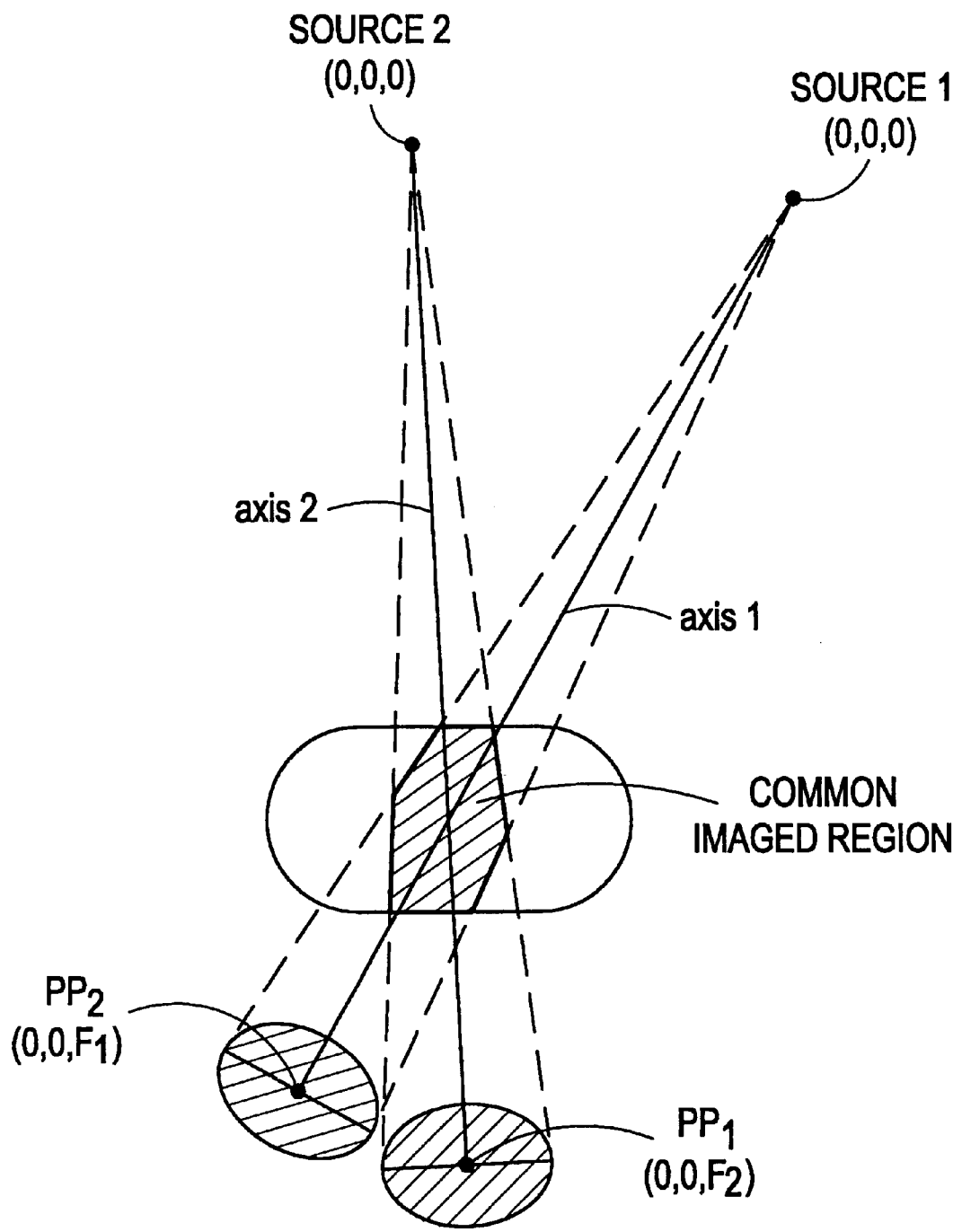
FIG. 7 illustrates camera calibrations corresponding to the fluoroscope poses illustrated in FIG. 1A and used for the operation illustrated in FIG. 5.

It will be recalled that the camera calibration described above models the camera for each shot. Each configuration of the C-arm defines a coordinate system in which the origin, (0,0,0) is defined by the location of the x-ray source. The principal point is located at (0,0,F) where F is the focal length. That is, the optical axis, or axis of the imaging beam, is aligned along the third axis. Such a situation is schematically illustrated in FIG. 7 for the two fluoroscope positions shown in FIG. 1A. If all the fluoroscope configurations are taken in the context of a common world-coordinate system, each of these configurations defines a unique optical axis. Ideally, the point in three-space where all these optical axes intersect would be visible and centered in all the projection images. Based on the assumption that the fluoroscopic images are acquired by approximately centering the region of interest, applicant defines a projection center of the imaged tissue volume from the ensemble of camera models, and uses this intersection point as the origin for a three-dimensional reconstruction. This is done by applying a coordinate determination module, which identifies the optical axis intersection point as the intersection of, or best fit to, the $N^2$ pairs of optical axes of the modeled cameras for the N poses. In practice, two facts should are addressed in computing the center of projection: (a) the optical axes of any two fluoroscope shots are usually somewhat skew, lying in separate, but substantially parallel planes, and do not really intersect in space, and (b) the two "intersection" points determined by two different pairs of axes also do not generally coincide exactly.

In order to address these problems, for situation (a), the processor incorporates a software condition check for skewness of lines. If the optical axes are skew, the processor defines the intersection point as a computed point that is halfway between the two lines. In order to address the situation (b), the processor takes the mean coordinates of the $N^2$ skew-intersection points determined in the first step as its common center of projection. Thus the cluster of points defined by the $N^2$ pairs of axes determines a single point. This point is defined as the origin of the tissue region for which reconstruction is undertaken.

It is also necessary to determine a set of coordinate axes for the volume data set. Preferably, the axial planes of the reconstruction are to be parallel to the plane of motion of the x-ray source. Applicant's presently preferred processing module computes the plane of motion of the x-ray source by fitting a least-squares solution to the poses of the x-ray source. Any two non-collinear vectors in this plane define a basis for this plane and serve as two of the axes for the coordinate system. The module also computes a normal to this plane to serve as the third coordinate axis. The coordinate axis computation may be done by using eigen-analysis of the covariance matrix of the coordinates of the optical centers (x-ray source locations) and the principal points in the world-coordinate system. These eigenvectors are then ordered in order of decreasing eigenvalue. The first two eigenvectors provide a basis for the axial plane of interest, and the third eigenvector provides the normal to this plane. This procedure thus provides all three coordinate axes for the three-dimensional reconstruction. This determination is fully automated, and requires only the tracker data and camera models determined by the processor when each shot is taken. Further background and details of implementation for applying the eigenanalysis technique to define coordinate axes may be found in reference texts, such as the 1984 textbook "Pattern Recognition" by J. Therrien.

Having determined a coordinate system for the reconstruction, the processor then filters and back-projects the image data to form a volume image data set, from which CT planes may be reconstructed or retrieved in a conventional manner. The back projection step may utilize fast or improved processes, such as the fast Feldkamp algorithm or other variant, or may be replaced by other suitable volume data reconstruction technique, such as the local or Lambda tomography method described by A. Louis and P. Maass in IEEE Transac. Med. Imag. 764–769, (1993) and papers cited therein.

Thus, a simple set of automated tracking elements combined with image processing operative on a fixed or tracked marker array provides accurate tool tracking fluoroscope images, or a set of geometrically accurate reconstructed or CT images from the shadowgraphic images of a C-arm or intraoperative fluoroscope. The nature of the multi-point marker-defined camera image model allows the processor to quickly register, reference to a common coordinate system and back project or otherwise reconstruct accurate volume image data, and the fast determination of a camera parameter model for each shot proceeds quickly and allows accurate tool display for intraoperative tool navigation and dynamic tracking, without requiring rigid frames or robotic assemblies that can obstruct surgery, and without the necessity of matching to an MRI or PET database to achieve precision. Furthermore in the preferred embodiment, the models, transformations and fitting to a coordinate system proceed from the tracker position measurements of the marker fixture relative to the patient or tool, rather than from an extrinsic fixed frame, reducing potential sources of cumulative errors and simplifying the task of registering and transforming to common coordinates. Applicant is therefore able to precisely track and display the tool in real time, and to produce accurate fluoro-CT images using a C-arm fluoroscope.

It will be understood that the description above relies upon tracking measurements made by tracking elements each fixed with respect to one of a few movable objects. As applied to the patient or tool, these tracking elements may be affixed by belts, frames, supports, clips, handles or other securing or orienting structures known in the art. In general, applicant's preferred tracking element is a magnetic field tracking element, which may be oriented and affixed in a rigid housing that allows it to secure to the structure to be tracked. Actual implementation of the system may involve a preliminary calibration procedure wherein the actual dimension, offset or relative position of the tool tip, the marker array or the like, with respect to the tool or array tracking element is permanently stored in a chip or non-volatile memory so that minimal or no set-up initialization is required during an imaging session. Similarly, when employing such magnetic tracking elements, a table of field or position corrections may be initially compiled for the tracking element mounted on the fluoroscope to assure that the tracking achieve a high level of accuracy over a broad field extending quite close to the image detector and C-arm structures. Additional reference sensor-type tracking elements or standards may also be provided as described in the aforesaid '980 patent, if desired to enhance the range, resolution or accuracy of the tracking system.

The calibration fixture has been described above as being preferably affixed to the image detector portion of the fluoroscope, where, illustratively one or several precision arrays of markers located along the imaging axis provide necessary data in the image itself to characterize the camera each time an image is taken. This location, with the markers in a single fixture, provides a high level of accuracy in determining the desired camera parameters, and enables tracking to proceed without obstructing the surgical field.

To the extent that the constraint of positioning the calibration fixture between the target tissue and the detector may limit flexibility in positioning the image detector near the patient, this may be addressed in other embodiments by having all or a portion of the marker array assembly implemented with markers located on or in a radiographic support table (75, FIG. 6) or other structure on which the patient or the imaged tissue portion is supported. In this case, the table or support itself, which is radiolucent, may have a thickness and structure that permits markers to be embedded at different depths. For example, it may be formed of a structural foam material as described above in regard to the marker fixture of FIG. 3A. Alternatively, the markers may be included in one or more sheets that fit within the x-ray sheet film tray of a conventional radiography table, or such marker sheets may be laminated to the bottom and/or top surfaces of the table. When affixed to the table or inserted in a registered or fixed fashion, the tracking element $T_2$ may then be attached anywhere on the rigid structure of the table itself, with suitable offsets stored in a fixed memory element of the system. In embodiments utilizing such markers in the table, the total angular range of the poses in which useful marker images will appear in the fluoroscope images may be restricted to somewhat under 180°. Furthermore, the image plane will generally not be parallel to the marker arrays, so a different set of computations is utilized by the processor to characterize the camera position and geometry. However, these computations involve straightforward camera modeling, and may be accelerated by also tracking the image detector with an additional element $T_2'$.

Figure 6:
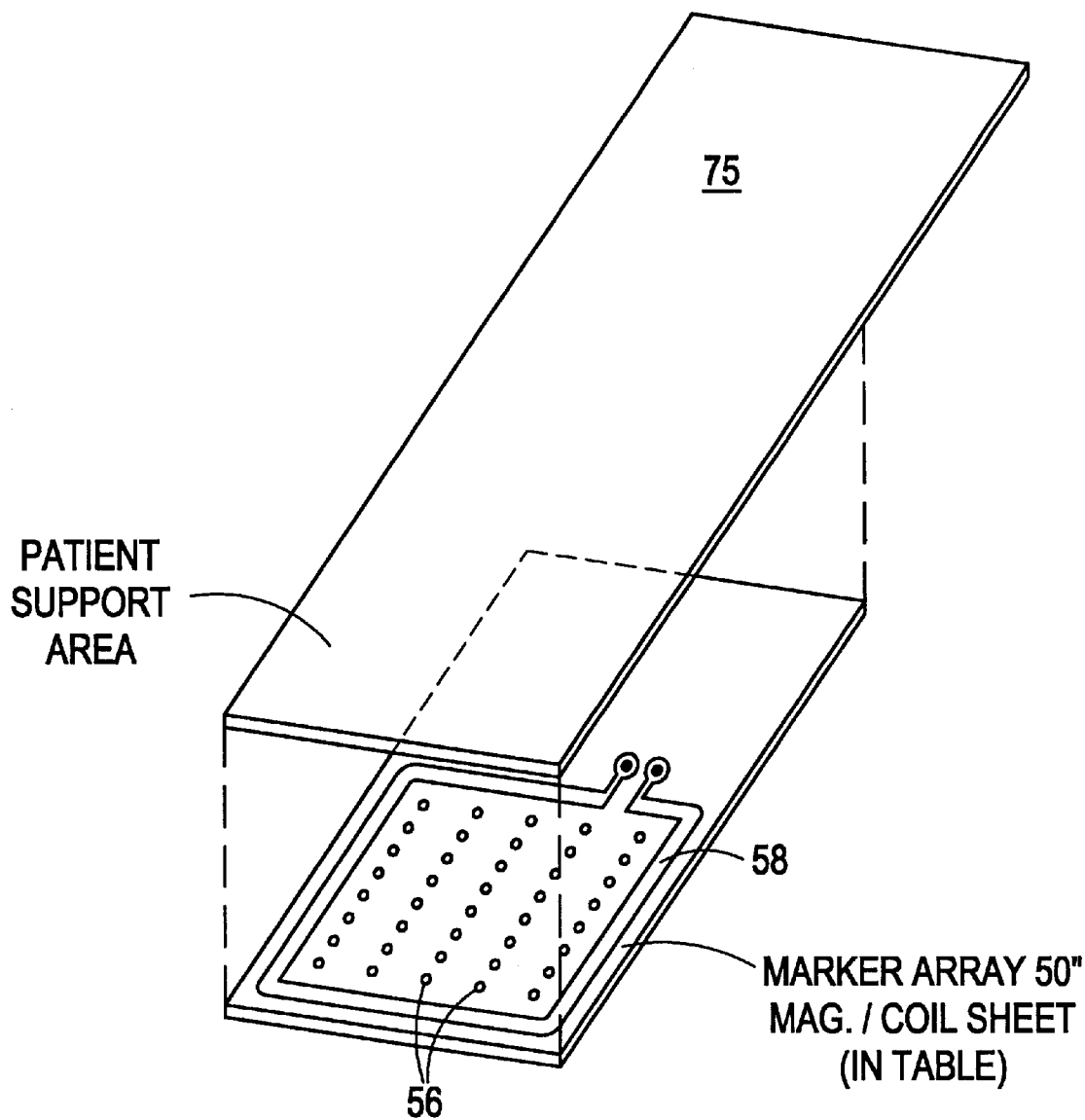
FIG. 6 illustrates a sheet fixture for use with the invention and having combined calibration and tracking elements.

The calibration fixtures of the invention as well as the embodiments having markers on or in the table may be implemented with one or more separately-made sheet structures. FIG. 6 shows elements of one such embodiment wherein a marker array 50" is formed as a pattern of metallized dots 56, which may be formed lithographically on a printed-circuit type sheet. As indicated schematically in this Figure, the sheet may also bear one or more lithographically-formed conductive loops 58, configured as a field generating or field sensing loop, for defining one or more elements of a magnetic tracking assembly. Three or more such patterned loops may be formed to constitute a basic electromagnetic generator or sensor that advantageously is precisely pre-aligned with respect to the coordinates of the markers 56 by virtue of its having been manufactured using a pattern lithography mask. The magnetic circuit loops may define magnetic multipoles for establishing or sensing position-tracking electromagnetic fields, or may, for example, include one or more coils of a system of Helmholtz coils for establishing a gradient field in the region where tracking is to occur. These may operate in conjunction with other coils disposed elsewhere for defining the tracking field, The implementation of magnetic tracking and radiographic marker elements on a sheet also allows plural sheets to be positioned and tracked separately for effecting the imaged based processing of the present invention.

In addition to the above described structure and operation of the invention, applicant contemplates system embodiments wherein a fluoro-CT data set is constructed as described above, and the fluoro-3D data set is then registered or correlated to an existing MRI, CT or PET 3D data set to form a fused set of images. These are then displayed on the system console 30 (FIG. 1) to provide enhanced patient information during surgery. Advantageously, the coordinates of the fluoro-CT images are known from the coordinates used in the reconstruction processing, while the correlation of the two different 3D image sets may proceed without reference to patient or other tracking coordinates, using any conventional 3D registration or correlation technique. This provides fast and effective fused image sets for surgical guidance or diagnostic evaluation.

Figure 8:
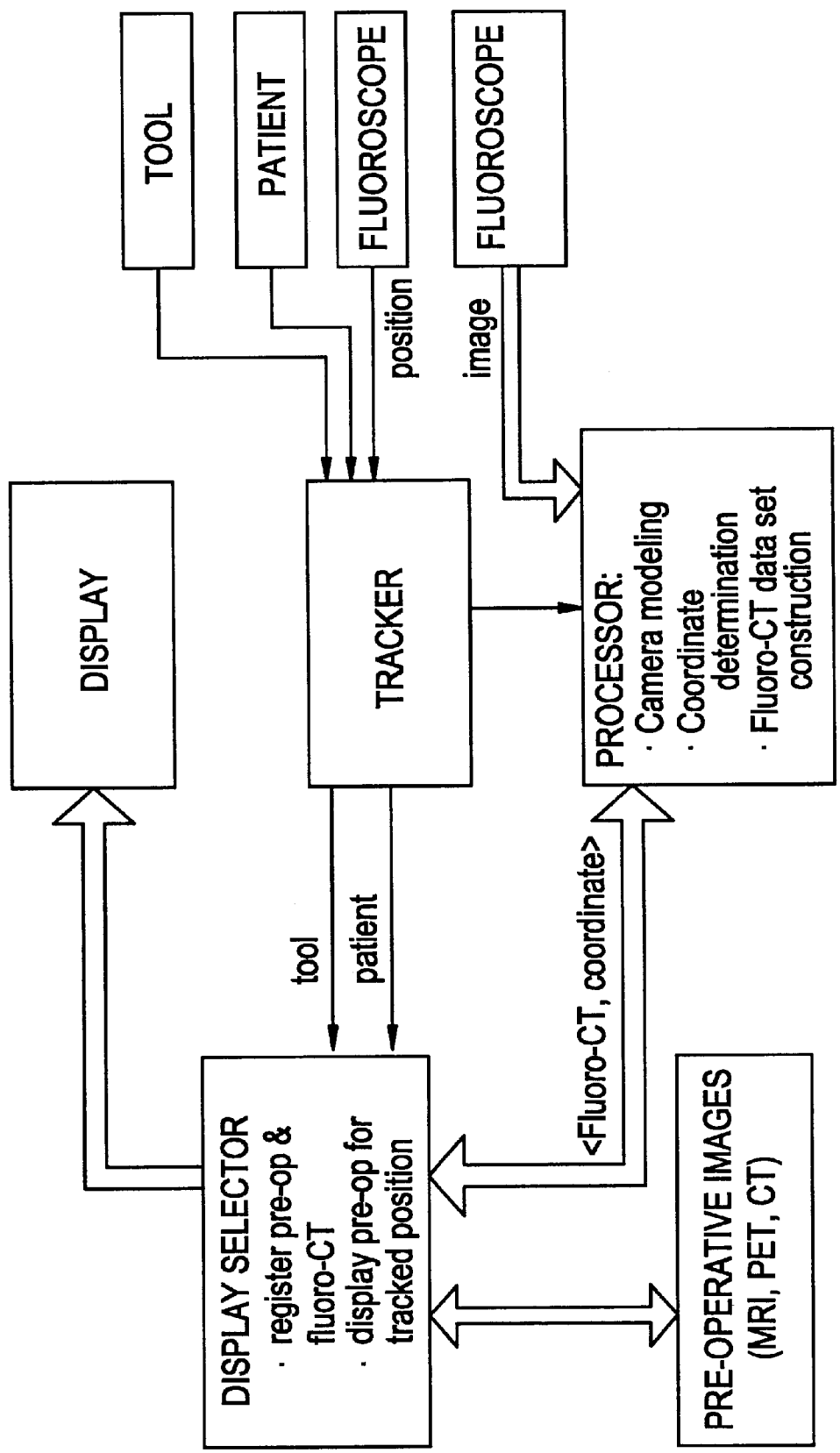
FIG. 8 illustrates operation of the system to register preoperative images to a patient.

Indeed, the system need not produce detailed fluoro-CT images, or need not display those images. Instead, the fluoro-CT images, or a lesser quality set of fluoro-CT images constructed from a faster (smaller) scan sequence of fluoro images, defined in tracker coordinates, may be produced and simply registered to a preoperative 3D data set in order to bring that preoperative image data set into the tracker coordinate system. In that case, the system applies this registration, and proceeds thereafter by simply tracking the patient and the tool, and displaying the appropriate preoperative images for each tracked location as shown in FIG. 8. Thus, in accordance with this aspect of the invention, the system provides an automated registration system for the intraoperative display of preoperative MRI, PET or CT images, without requiring placement or imaging of fiducials, without requiring the surgeon to initialize or set up a plurality of reference points, without requiring the surgeon to cut down to or expose a fixed skeletal registration feature, and without requiring immobilization of the patient in a frame or support. Instead, the intermediate fluoro-CT images are produced as part of an automated modeling and coordinatizing process, and both the production and the registration of these images to the preoperative data set may proceed entirely automated in software, for example, registering by mutual information (MI), feature correlation or similar process.

The invention being thus disclosed and illustrative embodiments depicted herein, further variations and modifications of the invention, will occur to those skilled in the art, and all such variations and modifications are considered to be within the scope of the invention, as defined by the claims appended hereto and equivalents thereof. Each of the patents and publications identified above is hereby incorporated by reference herein in its entirety.

What is claimed is:

1. A method for surgical imaging and display of the type including a fluoroscope x-ray source, imaging assembly, display and image processor, for displaying a fluoroscope image for surgical guidance, wherein the method comprises the steps of:

(i) positioning a defined set of markers disposed in a pattern so as to be imaged in each pose or view of the imaging assembly, said set of markers being fixed in pre-determined positions in a rigid carrier;

(ii) securing a first tracking element against motion with respect to the carrier so that determining position of said tracking element in a single measurement determines position of all the markers of the set;

(iii) identifying images of at least a subset of said markers in a first view;

(iv) applying said identified images and the determined marker positions to calibrate a camera model of the shot;

(v) repeating steps (i)–(iv) for each of a plurality of successive views taken in successively different fluoroscope positions; and (vi) registering image data from the plurality of views to a common coordinate system.

2. The method of claim 1, further comprising the steps of removing the identified images of markers from the first view to form an unobstructed view and displaying the unobstructed view.

3. The method of claim 1, further comprising the steps of
securing additional tracking elements to at least one object selected from among a patient and a tool so as to determine position of said object, and
positioning an image of object in the registered view.

4. The method of claim 1, further comprising the steps of
securing an additional tracking element to a patient to determine position of the patient, wherein said common coordinate system corresponds to a common region of imaged tissue in the patient, and
back-projecting image data from the plurality of views to form a fluoro-CT data set for said common region of tissue.

5. The method of claim 4, further comprising the step of registering said fluoro-CT data set to a set of preoperative CT, MRI or PET image data for said common region of tissue.

6. A system for surgical imaging and display of tissue structures of a patient, and including a display and an image processor for displaying such images in coordination with a tool image to facilitate manipulation of the tool during the surgical procedure, the system being configured for use with a fluoroscope such that at least one image in the display is derived from the fluoroscope at the time of surgery, and characterized in that the system comprises:
- a three-dimensional spatial fixture isometrically affixed to an imaging side of the fluoroscope for providing patterns of markers which are imaged in each fluoroscope image;
- a tracking assembly having at least two tracking elements operative to determine position of the fixture and patient, one of said tracking elements being secured against motion with respect to the spatial fixture so that determining position of said tracking element determines position of all the markers in a single measurement,
- a camera characterization module operative on data derived from images of the markers to model fluoroscopic imaging projection for each fluoroscope frame; and
- a CT image module connected for receiving a determination from the tracking assembly and the camera characterization module and operatively determining a common coordinate system in a region of imaged patient tissue for a plurality of fluoroscope poses,
- said CT image module being operative to form a fluoro-CT image data set representing said region of imaged patient tissue for reconstruction of image planes of tissue in said region.

7. The surgical imaging system of claim 6, wherein said system applies said tracking data and camera imaging parameters to project a representation of a tracked tool to a transformed display position on an untransformed but marker-free fluoroscope image.

8. The surgical imaging system of claim 6, wherein said CT image module applies back projection to a registered sequence of fluoroscope images to form said fluoro-CT image data set.

9. The surgical imaging system of claim 8, further comprising a module for correlating said fluoro-CT images with preoperative MRI, CT or PET image data to provide fused images for display.

10. A system for use with fluoroscope to effect registration of a preoperative 3D image data set to tissue of a patient, so as to display a preoperative image corresponding to a position of patient tissue tracked by a tracking assembly, such system comprising
- a tracking assembly including at least first and second tracking elements adapted for determination of fluoroscope and of patient tissue positions, respectively, in a coordinate system
- a processor operative with position information from the tracking assembly and with fluoroscope image data from a fluoroscope to construct a fluoro-CT data set representing a region of tissue in a patient, and
- a display image selector configured to operatively register a preoperative image set with said fluoro-CT data set to thereby assign tracked tissue coordinates to the preoperative image set whereby preoperative images are automatically registered to tracked positions of patient tissue.

* * * * *